United States Patent [19]

Eriksson

[11] Patent Number: 4,623,344
[45] Date of Patent: Nov. 18, 1986

[54] DOSING MEANS FOR A HYPODERMIC SYRINGE

[75] Inventor: Marja Eriksson, Upsala, Sweden

[73] Assignee: Duma AB, Sweden

[21] Appl. No.: 729,531

[22] Filed: May 2, 1985

[30] Foreign Application Priority Data

May 10, 1984 [SE] Sweden ............................ 8402527

[51] Int. Cl.$^4$ ............................................ A61B 19/00
[52] U.S. Cl. ...................................... 604/407; 141/27
[58] Field of Search .............. 604/208, 210, 211, 209, 604/407; 141/2, 27, 375

[56] References Cited

U.S. PATENT DOCUMENTS

| 2,861,570 | 11/1958 | Beecher | 604/407 |
| 3,237,660 | 3/1966 | Hill | 604/211 |
| 4,219,055 | 8/1980 | Wright | 141/27 |
| 4,434,820 | 3/1984 | Glass | 604/208 X |

FOREIGN PATENT DOCUMENTS 842198 7/1960 United Kingdom ................ 192/143

*Primary Examiner*—John D. Yasko
*Attorney, Agent, or Firm*—Ostrolenk, Faber, Gerb & Soffen

[57] ABSTRACT

A dosing means for facilitating the drawing of respective predetermined volumes of two liquids to be injected, in a single injection, into a hypodermic syringe comprises a first positioning element to hold the body of a removable hypodermic syringe, an axially displaceable plunger, and a second positioning element to hold a removable ampoule containing injection liquid. The two positioning elements are arranged so that the tip of the needle of the hypodermic syringe is inside the ampoule when the syringe and ampoule are located in the device. From the first positioning element a pin protrudes axially and carries first and second stops cooperating with the end of the plunger. When liquid is to be drawn in to the hypodermic syringe the plunger is drawn out until its end part meets the first stop. The first ampoule is then replaced by an ampoule containing a different type of liquid. The pin is then turned to move the first stop to leave a free passage for the end of the plunger, after which the plunger is drawn out further until its end comes into contact with the second stop. The hypodermic syringe now contains a correct mixture of the two liquids and is ready for injection.

17 Claims, 6 Drawing Figures

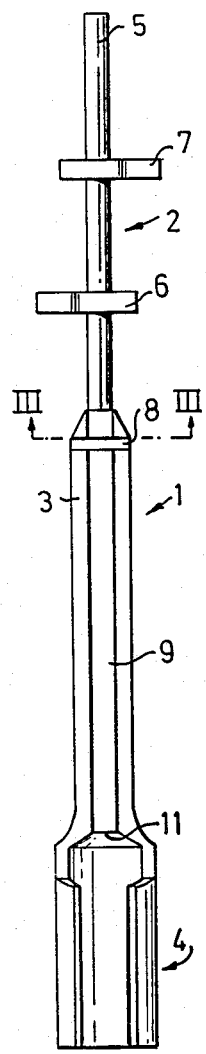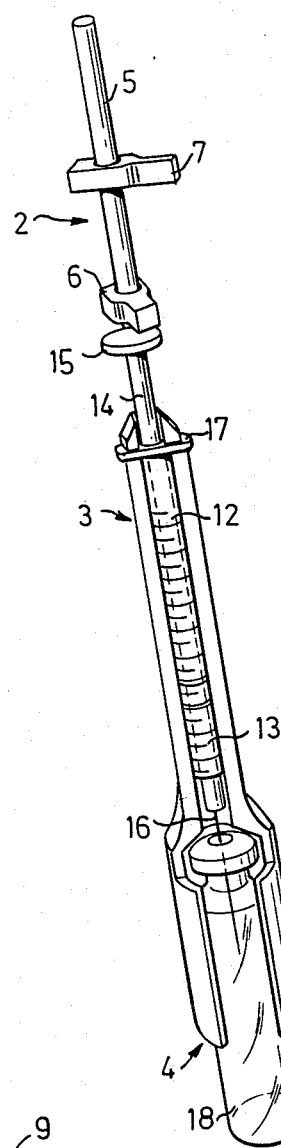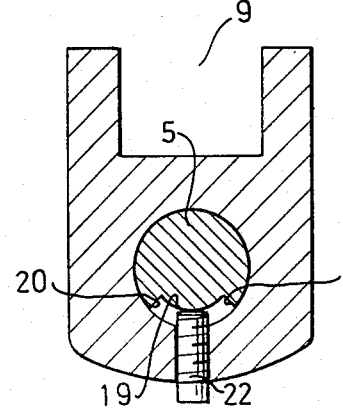
FIG.1
FIG.2
FIG.3

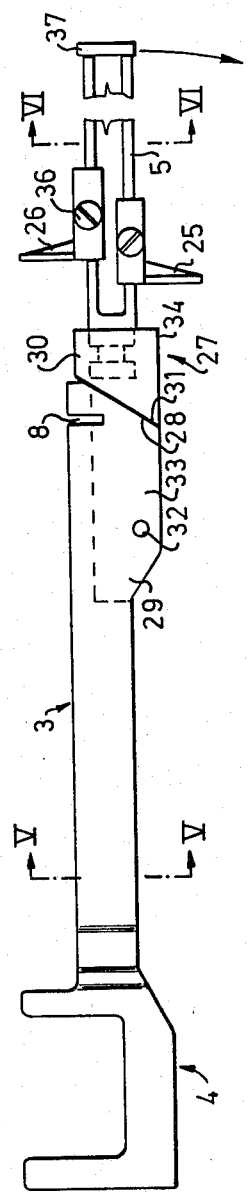
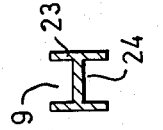
FIG.4
FIG.6
FIG.5

DOSING MEANS FOR A HYPODERMIC SYRINGE

BACKGROUND OF THE INVENTION

THE INVENTION relates to a dosing means for facilitating the drawing of a predetermined volume of a liquid, to be injected, into a hypodermic syringe having an axially displaceable plunger, the dosing means including a positioning element providing a formation to receive and locate the syringe body and means capable of limiting withdrawal of the syringe plunger to a first axial position with respect to said positioning element.

Such dosing means, known through U.S. Pat. No. 4,248,225, for instance, are of great help to diabetics who have poor eyesight, enabling them to measure the correct dose of insulin themselves.

However, very many diabetics nowadays require two different types of insulin, a quick-acting and a slow-acting insulin. This necessitates either two injections, which is undersirable in view of the difficulty and unpleasantness caused to the patient or, which is preferable, the incorporation of the desired doses of the two types of insulin into a single charge in a hypodermic syringe for administration to the patient in a single injection.

Conventional dosing means of the character referred to above are unsuitable for this purpose, i.e. for accurate measurement of respective doses of two liquids for injection drawn into a hypodermic syringe to form a single charge, since two different dosing means with different markings must be used, a first dosing means being used for the first dose and a new dosing means replacing the first dosing means after the first measured dose has been drawn into the hypodermic syringe, in order to assist in measurement of the second dose to be drawn up.

If the dosing means according to U.S. Pat. No. 4,248,255 is used, for instance, a first dosing means, marked for the first dose, must be applied on the finger grip of the hypodermic syringe, the needle of the syringe inserted in first ampoule, and the plunger drawn out until it comes into contact with a stop on the first dosing means, after which the first dosing means and ampoule are removed and a second dosing means, marked for the second dose, applied on the finger grip. An ampoule with a second injection composition is then applied over the tip of the hypodermic syringe after which the plunger is drawn out until it comes into contact with the stop of the second dosing means. It will be readily understood that besides the difficulty in dealing with two different dosing means, it is troublesome for a patient with poor eyesight and perhaps impaired coordination to carry out these different procedures correctly. There is also a considerable risk of the patient unintentionally moving the plunger during the exchanging procedure, so that some of the first injection liquid is lost and either the patient obtains an incorrectly proportioned dose or the entire procedure must be repeated.

SUMMARY OF THE INVENTION

The object of the present invention is to provide a dosing means which eliminates the drawbacks mentioned above, which can be used for most hypodermic syringes, including the preferred disposable type, and which enables even a person with poor eyesight, easily and with a few movements, to prepare a hypodermic syringeo doses of different injection liquids, these doses being measured with a greater degree of accuracy than is normally possible by means of a visual measurement.

According to the invention there is provided a dosing means for facilitating drawing a predetermined volume of liquid, to be injected, into a hypodermic syringe having an axially displaceable plunger projecting from the syringe, the dosing means including a first positioning element providing a formation to receive and locate the syringe body and means capable of limiting withdrawal of the syringe plunger to a first axial position with respect to the first positioning element, charcterised by means capable of limiting withdrawal of the syringe plunger to a second axial position with respect to the first positioning element, further from the first positioning element than the first axial position, whereby, in use, with such a hypodermic syringe mounted in the first positioning element, the plunger of the syringe can be drawn out, to draw a first liquid for injection into the syringe, until the axial movement of the plunger is limited at said first axial position, and subsequently the plunger of the syringe can be allowed to pass beyond said first axial position and can be drawn out further to draw a second liquid for injection into the syringe until the axial movement of the plunger is limited at said second position.

BRIEF DESCRIPTION OF THE DRAWINGS

The accompanying drawings show preferred embodiments of the invention, by way of example.

In the drawings:

FIG. 1 shows a first embodiment of a dosing means according to the invention, seen from the side, FIG. 2 shows the dosing means according to FIG. 1 in perspective, with a hypodermic syringe and an ampoule inserted, FIG. 3 shows a section along the line III—III in FIG. 1, on an enlarged scale, FIG. 4 shows a second embodiment of a dosing means according to the invention, seen from the side, FIG. 5 shows a section along the line V—V in FIG. 1, and FIG. 6 shows a section along the line VI—VI in FIG. 1.

DESCRIPTION OF THE PREFERRED EMBODIMENTS

FIGS. 1 and 2 show a dosing means 1 which comprises three main elements, namely a first positioning element 3 providing a formation to receive and locate the body of a hypodermic syringe 12 provided with an axially displaceable plunger 14, a second positioning element 4 providing a formation to receive and locate an ampoule 18 of liquid for injection, the element 4 being at one end of the element 3, and ajustable stops 6, 7 mounted on a rod or pin 5 carried by, and extending from the other end of the first positioning element 3 and arranged to cooperate with the plunger 14 protruding from the hypodermic syringe, in order to assist in the metering of predetermined dosing volumes of liquid to be drawn into the syringe as explained in more detail below.

The hypodermic syringe 12 removable inserted in the first positioning element 3 of the dosing means and shown in FIG. 2 is of the conventional, disposable type. It is made mainly of plastics and includes a cylindrical body 13 to hold the injection liquid, said body being provided at one end with a hypodermic syringe needle 16 and at the other end with a finger grip formed by a flange 17 protruding from the cylindrical body 13. A plunger 14 is axially movable in the cylindrical body 13 and comprises a plunger head with a seal abutting the inner wall of the cylinder 13. The plunger 14 has a free end part 15 which projects from the cylinder 13.

The second positioning element 4 of the dosing means in the embodiments shown is shaped to fit a cylindrical ampoule 18, partially enclosing it so that when the ampoule 18 is inserted in said positioning element 4, its penetratable sealing membrane is aligned exactly with the needle of the syringe fitted in the first positioning element 3. the second positioning element 4 is suitably provided with a stop means 11 limiting displacement of the ampoule 18 in the longitudinal direction.

The first positioning element 3 of the dosing means 1 is integral with the second positioning element 4 and provides a longitudinal groove 9 for the cylindrical body 13 of hypodermic syringe, the width of the groove being slightly greater than the diameter of the cylindrical body 13. The groove 9 thus retains hypodermic syringe laterally (except as regards lateral movement through the mouth of the groove 9 for insertion and removal of the syringe). The first positioning element 3 is provided with a notch or slot 8 adjacent its upper end to receive the flange 17 protruding from the cylindrical body 13 of the hypodermic syringe 12, whereby the syringe body is retained against axial movement relative to the positioning elements 3, 4. The notch 8 is located at such a distance from the stop 11 of the second positioning element 4, and the groove 9 has such a length, that the hypodermic syringe 16 extends into the space defined within the second positioning element 4 when the hypodermic syringee first positioning element 3 with flange 17 inserted in the notch 8.

The stops 6, 7 protrudes substantially radially from the pin 5. The pin 5, is rotatable in a bore in the element 3 and is provided, in the region within said bore, with a groove 19 extending around part of its circumference. A grub screw 22 projects into said bore and engages in the peripheral groove 19, said screw being inserted in a tapped hole extending from the outside of the element 3 to the bore. Axial movement of the pin 5 relative to the element 3 is limited by abutment of screw 22 with the axial flanks of the groove 19. The circumferential ends of the groove 9 form abutment faces or stops 20 and 21 which come into contact with the screw at the extremes of rotational movement of the pin 5, about its axis, in the element 3 so that the pin 5 can be moved rotationally between two positions determined by the said stops 20 and 21.

The stops 6, 7 are provided with through bores which receive the pin 5 as a free fit so that the stops 6, 7 can be slid along the pin for purposes of adjustment. The stops 6, 7 are provided with respective locking means enabling them to be locked to the pin 5 in their desired axial positions, each said locking means consisting of a locking screw screwed into a respective tapped hole in the respective stop 6, 7. Each said tapped hole extends radially from said bore through the respective stop 6, 7, the respective locking screw, when screwed in, engaging the pin 5 to clamp the pin and lock the respective stop 6, 7 relative to the pin. The first stop 6 is locked to the pin 5 in such an angular position that it is immediately opposite the end part 15 of the plunger 14 when one stop 21 in the groove 19 in pin 5 is in contact with the grub screw 22. The second stop 7 is locked to the pin 5 in such an angular position that it is in front of the end part 15 when the second stop 20 in the groove 19 of pin 5 is in contact with the grub screw 22. When the second stop 7, by virtue of the rotational position of pin 5, assumes a position opposite the plunger 14, the first stop 6 is in a position removed from the axial path of movement of the plunger 14, so that the end part 15 of the plunger can pass it unimpeded. The dosing means described functions in the following manner. A doctor or qualified person sets the dosing means in advance in accordance with the patent's requirements. To do this the locking means for the spacers 6, 7 must first be released. The stops 6, 7 are then set at suitable positions, corresponding to the desired dosage, on the cylindrical pin 5 and then locked to the pin. A check is then preferably made to ensure that correct doses are obtained.

In use, the patient places a hypodermic syringe 14 in its fully depressed position in the pre-set dosing means 1 so that flange 17 engages in notch 8. An ampoule with a first liquid is then fitted into the second positioning element 4, the hypodermic syringe 16 penetrating the ampoule membrane. Pin 5 is then turned so that the first stop 6 is immediately opposite the plunger 14. Plunger 14 is then drawn out until its end part 15 comes into contact with the stop 6. The hypodermic syringe 12, now contains the correct quantity of the first liquid. The first ampoule is then removed and a new ampoule containing the second liquid is placed in the second positioning element so that the needle 16 penetrates the membrane of the new ampoule. The pin 5 is then rotated until the second stop 20 in the peripheral groove 19 comes into contact with the grub screw 22. The second stop 7 is now immediately opposite the end part 15 and the first stop 6 has been moved out of the way, allowing free passage for the plunger 14. The plunger 14 is then withdrawn further until its end part 15 comes into contact with the stop 7. The hypodermic syringe contains the correct mixture of the two liquids, which can now be injected.

In FIGS. 4 to 6, like references to those used in FIGS. 1 to 3 denote corresponding parts.

In the second embodiment, shown in FIGS. 4 to 6, stops 25, 26 for pre-setting the doses are connected to first positioning element 3 by way of an intermediate element 27.

The first positioning element 3, in this embodiment, is a substantially H-section elongate member having two flanges 23 connected by a web 24 (FIG. 5), the groove 9 to receive a syringe body being defined on one side of web 24 between the flanges 23. Near the intermediate element 27, the flanges 23 are extended further from web 24 to provide cheeks 33 which are provided with aligned holes. The web 24 ends before the cheeks 33 so that a free space is provided between the cheeks 33 in the end portion of the positioning element 3. Each of the cheeks 33 terminates in an inclined abutment edge 28. The intermediate element 27 comprises a narrow, elongated portion 29, fitting freely between the cheeks 23 and provided with a hole which is aligned with the holes in the cheeks 33. The element 27 is pivotably mounted between the cheeks 33 by means of a pin 32, e.g. in the form of a rivet, which is passed through said aligned holes. A thicker portion 30 of the intermediate element 27 is integral with the narrow, elongated portion 29 and provides, on each side, inclined abutment faces 31, cooperating with the inclined abutment edges 28 of the cheeks 33 thereby limiting pivotal movement in one direction of the intermediate element 27 with respect to element 3, about pin 32. When the intermediate element 27 is pivoted in the other direction the underside 34 (as viewed in FIG. 4) of the thicker portion 30 of the intermediate element 27 will strike against the underside (as viewed in FIG. 4) of the positioning element 3, i.e. against the free edges of the flanges 23. In this way the angle of pivotal movement of the intermediate element 27 relative to element 3 is limited to about 180°. The upper side (as viewed in FIG. 4) of the narrow portion 29 of the intermediate element 27 is flat and forms an extension of the face of web 24 which faces into groove 9, being co-planar with said face when the abutment portions 28 of the cheeks 33 and the abutments 31 of the intermediate portion 27 contact each other in the position in which the dosing means is used. Thus in this second embodiment the dosing means is made collapsible from an extended use position to a non-use position, in which the dosing means takes up less space and can be more conveniently carried.

The intermediate element 27 is further provided with an axial bore in which the cylindrical end of a member 5' is rotatably received in the same way as that in which the pin 5 is mounted in the bore in element 3 in the embodiment of FIGS. 1 to 3, with; the member 5' being retained against axial movement in element 27 and limited in its rotational movement between two defined angular positions relative to member 27, in the same way as in the embodiment of FIGS. 1 to 3, that is to say, by a screw projecting into a groove formed in the part of member 5' within said bore, said groove extending only part of the way around the circumference of the member 5'. The part of member 5' projecting from member 27 of uniform 'H' section over most if its length as far as its free end, as shown in FIG. 6, comprising two flanges 35, connected by a central web. A sliding shoe 25, 26 is mounted on each flange 35 for sliding adjusting movement therealong. Each sliding shoe 25, 26, comprises a locking means, e.g. a locking screw 36, by means of which the sliding shoe 25, 26 can be locked in a desired axial position on the corresponding flange 35. Each shoe 25, 26 is also provided with a radially protruding stop. Each sliding shoe 25, 26, has an axially extending 'T',—section groove therethrough which accommodates the respective flange and the adjoining part of the web connecting the flanges. Each said 'T'-section groove is of a size, slightly larger than section of the respective flange 35 and adjacent the part of the connecting web. The shoes 25, 26 are pushed onto their respective flanges from the free outer end of member 5' during assembly of the device. A cover 37 can then be applied on the end portion of the member 5' to prevent shoes 25, 26 from sliding off the member 5'.

In use, the hypdermic syringe body is located in groove 9 with the flange 17 located in slots 8 and the respective ampoule located in element 4, in the same way as described in relation to FIGS. 1 to 3. The plunger of the syringe is then withdrawn, with the stop of the shoe 25 disposed in the path of the plunger end, until the end of the plunger engages the last-noted stop. The ampoule is then exchanged for an ampoule of the second liquid, and the member 5' rotated about its longitudinal axis relative to member 27 through 180° to move the shoe 25 out the path of the plunger end and to move the; stop on shoe 26 into the path of the plunger end, after which the plunger is withdrawn further until it engages the stop on shoe 26. The syringe is then ready for injection of the liquids. The peripheral groove in the cylindrical part of member 5', of course, in this embodiment, extends through somewhat more than 180° around this cylindrical part, so that the abutment screw (not shown) engages the ends of this groove at opposite ends of a 180° rotation of member 5'.

The invention is of course not limited to the embodiments shown in the drawings. Several other embodiments are feasibe within the scope of the invention. For example, the stops need not be arranged axially adjustably along the pin 5 or member 5' but may be permanently fixed thereto and made in one piece with the pin 5 or member 5' at the manufacturing stage, being positioned in accordance with certain standard doses determined in advance.

The means described above thus enables persons with poor eyesight, with a few simple movements, to draw up correct quantities of injection liquids into a hypodermic syringe. Furthermore this is achieved with a greater accuracy than is normally obtained with visual measurement.

I claim:

1. A dosing means for facilitating drawing a predetermined volume of liquid, to be injected, into a hypodermic syringe having an axially displaceable plunger projecting from the syringe, the dosing means including:
    a first positioning element providing a formation to receive and locate the syringe body,
    first limiting means capable of limiting withdrawal of the syringe plunger to a first axial position with respect to the first positioning element,
    second limiting means capable of limiting withdrawal of the syringe plunger to a second axial position with respect to the first positioning element, further from the first positioning that the first axial position, and
    a rotatable member, on which said first and second limiting means are mounted, means mounting said rotatable member for rotation relative to said first positioning element between a position in which said first limiting means lies in the path of movement of the free end of the plunger of the syringe located in said first positioning element, and a position in which said second limiting means lies in the path of movement of the free end of the plunger of the syringe so located and the first limiting means does not.

2. A dosing means according to claim 1 including a second positioning element provided at an end of the first positioning element, said second positioning element providing a formation to receive and locate removably a container of liquid for injection.

3. A dosing means according to claim 1 in which said first limiting means comprises a first stop and said second limiting means comprises a second stop, said first and second stops being capable of cooperating with the free end of the plunger.

4. A dosing means according to claim 3, including a pin, means mounting the pin in said first positioning element to extend therefrom, and means mounting said first stop and said second stop on said pin.

5. A dosing means according to claim 4, in which the pin is directly connected to the first positioning element.

6. A dosing means according to claim 3, including an intermediate element and means mounting said intermediate element on said first positioning element for pivotal movement with respect to the first positioning element, whereby the dosing means is collapsible.

7. A dosing means according to claim 1, including a supplementary stop element and further stop means on said rotatable member, limiting rotary movement of said rotatable member relative to the first positioning element by cooperating with said supplementary stop element.

8. A dosing means according to claim 7, including a support, a bore in said support, said rotatable member comprising an elongate pin having an axis and which is rotatable about its axis in said bore in said support, a groove in the pin, the ends of the groove forming abutments constituting said further stop means, said supplementary stop element comprising a screw extending into said support and projecting into said bore to engage in the peripheral groove for engagement with said ends of said groove.

9. A dosing means according to claim 1, including means for adjusting said first and second limiting means for adjustment of said first and second axial positions.

10. A dosing means according to claim 1 including an intermediate element and means mounting said intermediate element on said first positioning element for pivotal movement with respect to the first positioning element.

11. A dosing means according to claim 10, including means for adjusting said first and second limiting means for adjustment of said first and second axial positions.

12. A dosing means according to claim 10, including a supplementary stop element and further stop means on said rotatable member, limiting rotary movement of said rotatable member relative to the first positioning element by cooperating with said supplementary stop element.

13. A dosing means according to claim 12 including a support, a bore in said support, said rotatable member comprising an elongate pin having an axis and which is rotatable about its axis in said bore in said support, a groove in the pin, the groove extending part-way around the periphery of the pin, the ends of the groove forming abutments constituting said further stop means said supplementary stop element comprising a screw extending into said support and projecting into said bore to engage in the peripheral groove for engagement with said ends of said groove.

14. A dosing means according to claim 3 including a supporting member, means mounting said first and second stops on said supporting member for displacement along the supporting member for adjustment of the axial positions of said stops, and means for fixing said first and second stops at desired axial positions along said supporting member.

15. A dosing means according to claim 14, in which said means for fixing said stops comprise screws passing through said stops and engageable with said supporting member whereby the stops can be clamped tightly to the supporting member.

16. A dosing means according to claim 7 including a supporting member carried by said first positioning element and in which said first and second stops are made in one piece with said supporting member.

17. A dosing means according to claim 1, wherein the first positioning element is provided with a notch in which a flange protruding from the barrel of a hypodermic syringe can engage.

* * * * *